United States Patent [19]
Bhatnagar et al.

[11] Patent Number: 6,114,357
[45] Date of Patent: Sep. 5, 2000

[54] HEMOREGULATORY COMPOUNDS

[75] Inventors: Pradip Kumar Bhatnagar, Exton; Dirk Andries Heerding, Malvern, both of Pa.; Michael Hartmann; Johann Hiebl, both of Linz, Austria; Peter Kremminger, Asten, Austria; Franz Rovenszky, Linz, Austria

[73] Assignees: SmithKline Beecham Corporation, Philadelphia, Pa.; Nycomed Austria GmbH, Linz, Austria

[21] Appl. No.: 09/068,641

[22] PCT Filed: Nov. 12, 1996

[86] PCT No.: PCT/US96/18340

§ 371 Date: Feb. 9, 1999

§ 102(e) Date: Feb. 9, 1999

[87] PCT Pub. No.: WO97/17968

PCT Pub. Date: May 22, 1997

Related U.S. Application Data

[60] Provisional application No. 60/006,639, Nov. 13, 1995.

[51] Int. Cl.[7] .................. A61K 31/455; C07D 401/12
[52] U.S. Cl. ............................ 514/332; 546/262
[58] Field of Search .............. 546/262; 514/332

[56] References Cited

U.S. PATENT DOCUMENTS 3,917,626  11/1975  Edward ................. 260/295.5
5,360,806  11/1994  Toki et al. .............. 514/318

FOREIGN PATENT DOCUMENTS 0 324 521  7/1989  European Pat. Off. .

*Primary Examiner*—Fiona T. Powers
*Attorney, Agent, or Firm*—Linda E. Hall; Stephen A. Venetainer; Charles M. Kinzig

[57] ABSTRACT

Novel compounds of general formula (1), which have hemoregulatory activities and can be used to stimulate haematopoiesis and for the treatment of viral, fungal and bacterial infectious diseases.

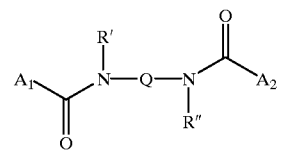

(I)

14 Claims, No Drawings

HEMOREGULATORY COMPOUNDS

This appln is a 371 of PCT/US96/18340 filed Nov. 12, 1996 and also claim the benefit of U.S. Provisional No. 60/006,639 filed Nov. 13, 1995.

FIELD OF THE INVENTION

The present invention relates to novel compounds which have hemoregulatory activities and can be used to stimulate haematopoiesis and for the treatment of viral, fungal and bacterial infectious diseases.

BACKGROUND OF THE INVENTION

The haematopoietic system is a life-long cell renewal process whereby a defined stem cell population gives rise to a larger population of mature, differentiated blood cells (Dexter TM. Stem cells in normal growth and disease, Br Med J 1987; 195:1192–1194) of at least nine different cell lineages (erythrocytes, platelets, eosinophils, basophils, neutrophils, monocytes/macrophages, osteoclastes and lymphocytes) (Metcalf D. The Molecular Control of Blood Cells, 1988; Harvard University Press, Cambridge, Mass.). The stem cells are also ultimately responsible for regenerating the bone marrow following treatment with cytotoxic agents or following bone marrow transplantation.

The major dose-limiting toxicities of most standard antineoplastic drugs are related to bone marrow suppression, which if severe and prolonged, can give rise to life-threatening infectious and haemorrhagic complications. Myelosuppression is predictable and has been reported to be dose-limiting in greater than 50% of single-agent Phase I trials cytotoxic compounds (Merrouche Y, Catimel G, Clavel M. Haematopoietic growth factors and chemoprotectants; should we move toward a two-step process for phase I trials in oncology? Ann Oncol 1993; 4:471–474). The risk of infection is directly related to the degree of myelosuppression as measured by the severity and duration of neutropenia (Brody G. P., Buckley M., Sathe Y. S., Freireich E. J. Quantitative relationship between circulating leukocytes and infections with acute leukemia Ann In Med 1965; 64:328–334).

The control of haematopoiesis involves the interplay of a variety of cytokines and growth factors during various stages of the haematopoietic cascade, including early pluripotent stem cells and mature circulating effector cells. These regulatory molecules include granulocyte colony stimulating factor (G-CSF), granulocyte-macrophage stimulating factor (GM-CSF), macrophage-colony stimulating factor (M-CSF), and a variety of interleukines which have overlapping, additive and synergistic actions which play major roles in host defence. Mechanistically, this is accomplished by enhancing the production of granulocytes and macrophages, as well as by the activation of effector cell functions (Moore MAS. Haematopoietic growth factor interactions: in vitro and in vivo preclinical evaluation. Cancer Surveys 1990; 9:7–80). These coordinated activities support optimal host defences which are necessary for fighting bacterial, viral and fungal infections.

Strategies to prevent or reduce the severity of neutropenia and myelotoxicity include the use of haematopoietic growth factors and/or other haematopoietic cytokines. Such treatments are becoming common practice, in that they offer the potential of increased doses of cytotoxic agents that may improve the therapeutic efficacy if antineoplastic agents, and reduce the morbidity associated with their use (Steward WP. Granulocyte and granulocyte-macrophage colony stimulating factors, Lancet 1993; 342:153–157). Clinical studies have demonstrated the G-, GM- and/or M-CSF may reduce the duration of neutropenia, accelerate myeloid recovery and reduce neutropenia-associated infections and other infectious complications in patients with malignancies who are receiving cytotoxic chemotherapy or in high infectious-risk patients following bone marrow transplantation (Steward WP. Granulocyte and granulocyte-macrophage colony stimulating factors, Lancet 1993; 342:153–157 and Munn D. H., Cheung NKV. Preclinical and clinical studies of macrophage colony-stimulating factor. Semin Oncol 1992; 19:395–407).

We have now found certain novel compounds which have a stimulative effect on myelopoietic cells and are useful in the treatment and prevention of viral, fungal and bacterial diseases.

SUMMARY OF THE INVENTION

This invention comprises compounds, hereinafter represented as Formula (I), which have hemoregulatory activities and can be used to stimulate haematopoiesis and in the prevention and treatment of bacterial, viral and fungal diseases.

These compounds are useful in the restoration of leukocytes in patients with lowered cell counts resulting from a variety of clinical situations, such as surgical induced myelosuppression, AIDS, ARDS, congenital myelodysplacis, bone marrow and organ transplants; in the protection of patients with leukopeaia from infection; in the treatment of severely burned patients and in the amelioration of the myelosuppression observed with some cell-cycle specific antiviral agents and in the treatment of infections in patients who have had bone marrow transplants, especially those with graft versus host disease, in the treatment of tuberculosis and in the treatment of fevers of unknown origin in humans and animas. The compounds are also useful in the treatment and prevention of viral, fungal and bacterial diseases, particularly Candida, Herpes and hepatitis in both immunosuppressed and "normal" subjects.

These compounds may also be used in combination with the monomers of co-pending U.S. application Ser. No. 07/799,465 and U.S. Pat. No. 4,499,081, incorporated by reference herein, to provide alternating peaks of high and low activity in the bone marrow cells, thus augmenting the natural circadian rhythm of haematopoiesis. In this way, cytostatic therapy can be given at periods of low bone marrow activity, thus reducing the risk of bone marrow damage, while regeneration will be promoted by the succeeding peak of activity.

This invention is also a pharmaceutical composition, which comprises a compound of Formula (I) and a pharmaceutically acceptable carrier.

This invention further constitutes a method for stimulating the myelopoietic system of an animal, including humans, which comprises administering to an animal in need thereof, an effective amount of a compound of Formula (I).

This invention also constitutes a method for preventing and treating viral, fungal and bacterial infections including sepsis, in immunosuppressed and normal animals, including humans, which comprises administering to an animal in need thereof, an effective amount of a compound of Formula (I).

DETAILED DESCRIPTION OF THE INVENTION

The compounds of the invention are represented by structural Formula I

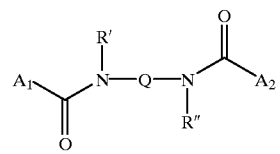
(I)

wherein:

A$_1$ and A$_2$ independently from each other denote a group Z—(CH$_2$)$_k$—(NR''')$_q$ wherein: Z is a 4–10 membered mono- or bicyclic heterocyclic ring system containing up to four heteroatoms N, O, S in the ring in which at least one heteroatom is N, and wherein the ring is substituted or unsubstituted by one or two C$_{1-4}$alkyl, F, Cl, Br, I, C$_{1-4}$ alkoxy, (CH$_2$)$_m$R$_4$, oxo, oxime, O—C$_{1-4}$alkyloxime, hydroxy, N(R$_3$)$_2$, acylamino or aminoacyl groups, 8, 9, 10 membered monocyclic ring systems being excluded;

k is an integer from 0 to 4;

R''' denotes hydrogen, C$_{1-4}$-alkyl or C$_{1-4}$-alkylcarboxylic acid;

q is an integer from 0 to 1;

R' and R' are independently hydrogen, C$_{1-4}$alkylC(O)R$_4$, C$_{1-4}$alkyl or R' and R'' are benzyl which is optionally substituted by one or two C$_{1-4}$alkyl, C$_{1-4}$alkoxy, F, Cl, I, Br, OH, or N(R$_3$)$_2$;

Q denotes a group

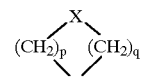

wherein:

B$_1$ denotes halogen, —(CH$_2$)m—CN, —(CH$_2$)$_{m+1}$—R$^2$, —(CH$_2$)$_m$—R$^3$, —(CH$_2$)m—COR$^2$ or —(CH$_2$)$_m$—COR$^3$; where R$^2$ independently denotes —OR$^3$, —N(R$^3$)$_2$, —SR$^3$;
R$^3$ is independently hydrogen, C$_1$—C$_4$-alkyl or benzyl;
m is independently an integer from 0 to 4;
C$_1$ denotes halogen, —(CH$_2$)$_n$—CN, —(CH$_2$)$_{n+1}$—R$^4$, —(CH$_2$)$_n$—R$^5$, —(CH$_2$)$_n$—COR$^4$ or —(CH$_2$)$_n$—COR$^5$;
R$^4$ independently denotes —OR$^5$, —N(R$^5$)$_2$, —SR$^5$;
R$^5$ is independently hydrogen, C$_1$—C$_4$-alkyl or benzyl;
n is independently an integer from 0 to 4;
B$_2$ denotes halogen, —(CH$_2$)$_p$—CN, —(CH$_2$)$_{k+1}$—R$^6$, —(CH$_2$)$_k$—R$^7$, —(CH$_2$)$_k$—COR$^6$ or —(CH$_2$)$_k$—COR$^7$;
R$^6$ independently denotes —OR$^7$, —N(R$^7$)$_2$, —SR$^7$;
R$^7$ is independently hydrogen, C$_1$—C$_4$-alkyl or benzyl;
k is independently an integer from 0 to 4;
C$_2$ denotes halogen, —(CH$_2$)$_s$—CN, —(CH$_2$)$_{s+s}$—R$^8$,—(CH$_2$)$_s$,—R$^9$, —(CH$_2$)$_s$—COR$^8$ or —(CH$_2$)$_s$—COR$^9$; where R$^8$ independently denotes —OR$^9$, —N(R$^9$)$_2$, —SR$^9$;
R$^9$ is independently hydrogen, C$_1$—C$_4$-alkyl or benzyl;
s is independently an integer from 0 to 4;
D is (CH$_2$)$_i$; in which up to two carbons are optionally gem-substituted by R$^{10}$ and R$^{11}$; where R$^{10}$ and R$^{11}$ are independently C$_{1-4}$alkyl, C$_{2-4}$alkenyl, C$_{2-4}$alkynyl; all of which may be substituted by one or two C$_{1-4}$alkyl, OH, F, Cl, Br, I, N(R$^{12}$)$_2$, (R$^{12}$)$_2$NC(O)—, —(CH$_2$)$_s$R$^{13}$, —(CH$_2$)$_s$R$^{12}$, —(CH$_2$)$_s$COR$^{13}$, or —(CH$_2$)$_s$C(O)R$^{12}$;

or R$^{10}$ and R$^{11}$ are F, Cl, or Br;
or R$^{10}$ and R$^{11}$ may together form a cyclic or heterocyclic ring of Formula (Ia):

$$\underset{B_1}{\overset{X}{(CH_2)_p\diagdown(CH_2)_q}}$$ (Ia)

in which p and q are independently an integer from 0 to 3; provided p and q are not both 0;
X is O, S, CH$_2$ or N(R$^{12}$);
R$^{12}$ is independently hydrogen, C$_{1-4}$-alkyl or benzyl;
R$^{13}$ is independently OR$^{12}$, N(R$^{12}$)$_2$ or SR$^{12}$;
i is an integer from 3 to 8;
with the proviso that B$_1$ is not identical to C$_1$ and B$_2$ is not identical to C$_2$;

A$_1$≠A$_2$;

B$_1$≠B$_2$;

C$_1$≠C$_2$;

B$_1$≠C$_1$; and

B$_2$≠C$_2$;

and pharmaceutically acceptable salts thereof.

Z in the above Formula (1) denotes an optionally substituted pyrrolyl, isopyrrolyl, pyrazolyl, isoimidazolyl, triazolyl, iosxazoly, oxazolyl, thiazolyl, isothiazolyl, oxadiazolyl, pyridinyl, pyridazinyl, pyrimidinyl, pyrazinyl, pyrrolidinyl, piperazinyl, triazinyl, morpholinyl, indolyl, indoleninyl, isobenzazolyl, pyrindinyl, ioindazolyl, indoxazinyl, benzoxazolyl, quinolinyl, isoquinolinyl, cinnolinyl, quinazolinyl, naphthyridinyl, pyridopyridinyl, tetrahydroquinolinyl, tetrahydroisoquinolinyl, quinoxalinyl, indolinyl, pyrrolidonyl, imidazolyl, imidazolidinyl, imidazolinyl, piperidyl, tetrazolyl, quinuclidinyl, azetidinyl, or purinyl;

Possible substituents for Z are C$_{1-4}$-alkyl, C$_{1-4}$-alkoxy, C$_{1-4}$-alkoxy—C$_{1-4}$-alkyl, oxo, oxime, O—C$_{1-4}$-alkyloxime, hydroxy, amino, C$_{1-4}$-alklamino, di-C$_{1-4}$-alkylamino, acylamino and aminoacyl.

R$^3$, R$^5$, R$^7$ and R$^9$ independently denote hydrogen, methyl, ethyl, propyl, i-propyl, butyl and benzyl.

Preferred compounds are those wherein Z is pyridinyl, pyrimidinyl, pyrazinyl, pyridazinyl, quinolinyl, tetrahydroquinolinyl, azetidinyl, or pyrrolidinyl; R$^{10}$ and R$^{11}$ are C$_{1-4}$alkyl, substituted by C$_{1-4}$ alkyl, OH, N(R$^{12}$)$_2$, —(CH$_2$)$_s$R$^{13}$, or —(CH$_2$)$_s$C(O)R$^{12}$; or R$^{10}$ and R$^{11}$ may together form a cyclic or heterocyclic ring of Formula (Ia) wherein X is O, S, or CH$_2$, and p and q are 1–3; R$^{12}$ is hydrogen or C$_{1-4}$alkyl; R$^{13}$ is OR$^{12}$ or N(R$^{12}$)$_2$.

More preferred compounds are those wherein Z is 2-pyridinyl, 2-pyrimidinyl, 2-pyrazinyl, 2-pyrrolidon-5-yl, or 2-pyrrolidinyl; R$^{10}$ and R$^{11}$ are C$_{1-2}$ alkyl, substituted by C$_{1-2}$alkyl, OH, N(R$^{12}$)$_2$, or —(CH$_2$)$_s$R$^{13}$; or R$^{10}$ and R$^{11}$ may together form a heterocyclic ring of Formula (Ia) wherein X is O; and p and q are 1 or 2; R$^{12}$ is hydrogen or C$_{1-4}$alkyl; and R$^{13}$ is OR$^{12,}$ or N(R$^{12}$)$_2$.

Preferred substituents for Z are methyl, ethyl, methoxy, methoxymethyl, oxo, oxime, hydroxy, amino, ethylamino or dimethylamino.

Preferred groups R', R'', B$_2$ and C$_2$ are hydrogen, methyl and ethyl.

Alkyl groups may be straight or branched.

The compounds of the present invention may contain one ore more asymmetric carbon atoms and may exist in racemic and optically active forms. All the compounds and diastereomers are contemplated to be within the scope of the present compounds.

METHOD OF PREPARATION

Compounds of Formula (I) wherein E, R', R", R'", $C_1$, $C_2$, $B_1$, $B_2$, $A_1$, $A_2$, Z, k, l, m, n, p, x and y are defined as in Formula (I) are prepared by methods analogous to those described in Scheme 1.

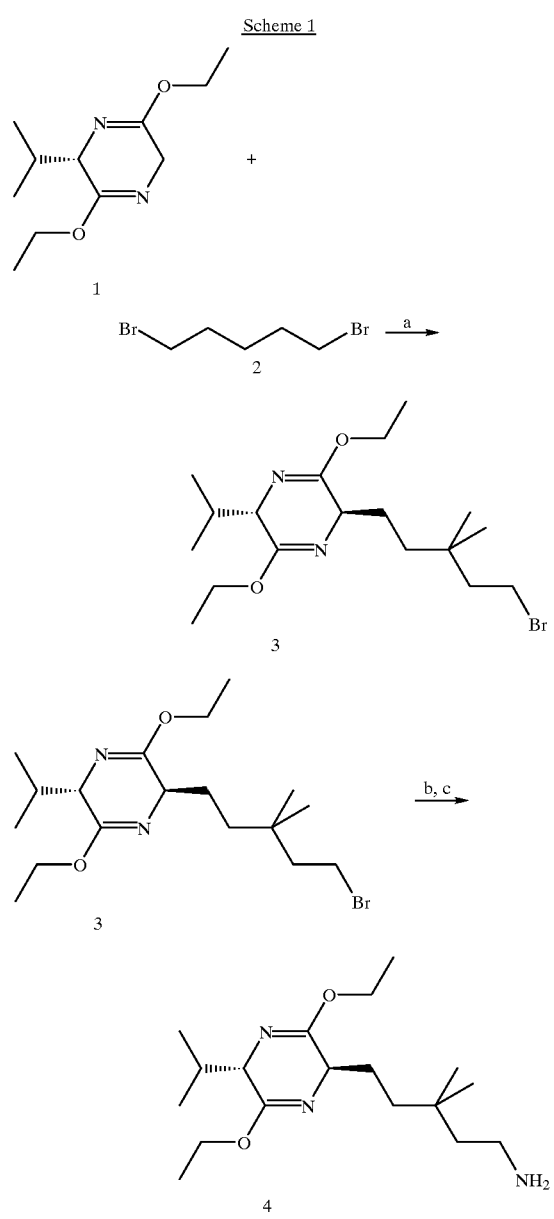
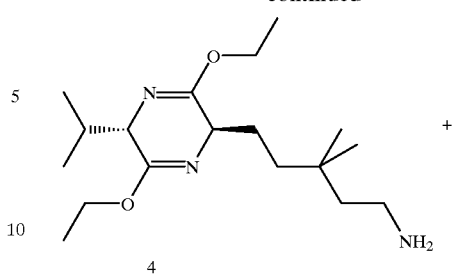
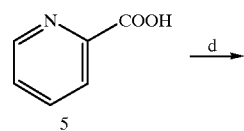
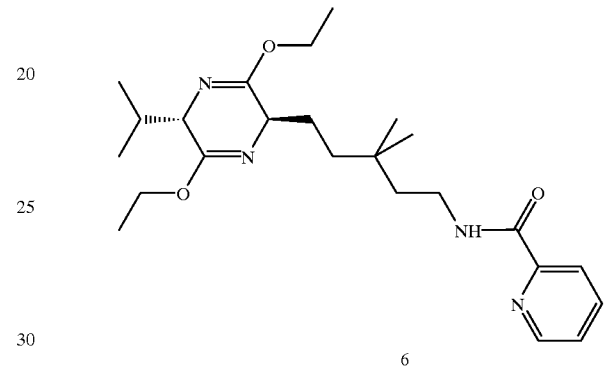
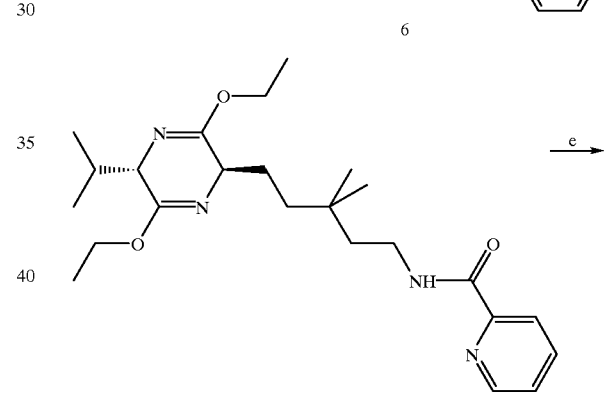

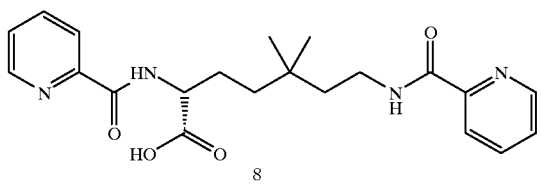

a) butyllithium, THF;
b) NaN₃, NBu₄L DMF;
c) triphenylphosphine, H₂O/THF;
d) DMAP, HOBt, EDC, CH₂Cl₂;
e) conc. HCl, dioxane/EtOH;
f) NaOH, dioxane/H₂O/EtOH One equivalent of (2S)-2,5-dihydro-3,6-diethoxyisopropylpyrazine (1 in Scheme 1) is coupled with an appropriate dielectrophile, such as 2 in Scheme 1, using a strong base (such as butyllithium) in a suitable solvent (such as THF) to give 3 in Scheme 1. Chemical group transformation with NaN₃ and NBu₄I in a suitable solvent (such as DMF) and subsequent reduction of the resulting azide with triphenylphosphine in suitable polar protic solvents (such as H₂O/THF) gives 4 in Scheme 1, which is then acylated with an appropriate heterocyclic acid, such as 5 in Scheme 1, using an activating agent (such as EDC) in an aprotic polar solvent (such as CH₂Cl₂). Hydrolysis and opening of the pyrazine-ring under standard acidic conditions (such as conc. HCl) in a suitable solvent (such as dioxane/ethanol) and subsequent acylation of the resulting amine according to method d) gives 7 in Scheme 1. Optional hydrolysis of the ester under standard basic conditions (such as NaOH) in a suitable solvent (such as dixane/ethanol) furnishes the product 8 in Scheme 1.

In order to use a compound of the Formula (I) or a pharmaceutically acceptable salt thereof for the treatment of humans and other mammals it is normally formulated in accordance with pharmaceutical practice as a pharmaceutical composition.

According to a still further feature of the present invention there are provided pharmaceutical compositions comprising as active ingredient one or more compounds of Formula (I) as herein before defined or physiologically compatible salts thereof, in association with a pharmaceutical carrier or excipient. The compositions according to the invention may be presented for example, in a form suitable for oral, nasal, parenteral or rectal administration.

As used herein, the term "pharmaceutical" includes veterinary applications of the invention. These peptides may be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline and water. Solid carriers include starch, lactose, calcium sulfate dihydrate, terra alba, magnesium stearate or stearic acid, talc, pectin, acacia, agar or gelatin. The carrier may also include a sustained release material such as glyceryl monostearate or glyceryl distearate, alone or with a wax. The amount of solid carrier varies, but, preferably will be between about 20 mg to about 1 g per dosage unit. The pharmaceutical preparations are made following the conventional techniques of pharmacy involving milling, mixing and filling for hard gelatin capsule forms. Capsules containing one or several active ingredients may be produced, for example, by mixing the active ingredients with inert carriers, such as lactose or sorbitol, and filling the mixture into gelatin capsules. Organ specific carrier systems may also be used.

Alternately pharmaceutical compositions of the peptides of this invention or derivatives thereof, may be formulated as solutions of lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, standard 5% dextrose in water or buffered sodium or ammonium acetate solution. Such formulation is especially suitable for parenteral administration, but may also be used for oral administration and contained in a metered dose inhaler or nebulizer for insufflation. It may be desirable to add excipients such as polyvinylpyrrolidone, gelatin, hydroxycellulose, acacia, polyethylene glycol, mannitol, sodium chloride or sodium citrate.

For rectal administration, a pulverized powder of the peptides of this invention may be combined with excipients such as cocoa butter, glycerin, gelatin or polyethylene glycols and molded into a suppository. The pulverized powders may also be compounded with oily preparation, gel, cream or emulsion, buffered or unbuffered, and administered through a transdermal patch.

Nasal sprays may be formulated similarly in aqueous solution and packed into spray containers either with an aerosol propellant or provided with means for manual compression.

Dosage units containing the compounds of this invention preferably contain 0.05–50 mg, for example 0.05–5 mg of the compound of Formula (I) or of the salt thereof.

According to a still further feature of the present invention there is provided a method of stimulation of myelopoiesis which comprises administering an effective amount of a pharmaceutical composition as hereinbefore defined to a subject No unacceptable toxicological effects are expected when compounds of the invention are administered in accordance with the present invention.

The biological activity of the compounds of Formula (I) is demonstrated by the following tests.

Induction of Hematopoietic Synergistic Activity in Stromal Cells

The murine bone marrow derived from stromal cell line C6.4 is grown in 12 well pates in RPMI 1640 with 10% FBS. Upon reaching confluence, the C6.4 cells are washed and the media exchanged with fresh RPMI 1640 without FBS. Confluent cell layers of murine C6.4 cells are treated with compound. Cell free supernatants are collected 18 hours later. Supernatants are fractionated with a Centricon-30 molecular weight cut-off membrane. C6.4 cell hematopoietic synergistic factor (HSF) activity is measured in a murine CFU-C assay.

CFU-C Assay

Bone marrow cells are obtained from C57B1/6 female mice and suspended in RPMI 1640 with 10% FBS. Bone marrow cells (7.5E+4 cells/mL) are cultured with sub optimal levels of CFU plus dilutions of test C6.4 cell 30K-E supernatants from above in a standard murine soft agar CFU-C assay. Cell aggregates >50 cells are counted as colonies. The number of agar colonies counted is proportional to the amount of HSF present within the C6.4 bone marrow stromal line supernatant Effector Cell Function Assay Female C57B 1 mice are administered test compound PO daily for 8 days. Resident peritoneal exudate cells (PEC) utilized ex vivo from treated or untreated mice are harvested with cold calcium and magnesium-free DPBS supplemented with heparin and antibiotics within 2–4 hours following the last injection. Adherent PEM populations are prepared by incubating standardized PEC suspensions in microtiter dishes for 2 hours at 37° C. (5% $CO_2$) and removing nonadherent cells by washing the wells with warm buffer.

The superoxide dismutase-inhibitable (SOD) superoxide released by effector cells in response to a in vitro stimulation by phorbol myristate acetate (PMA) (100–200 nM) or pre-opsonized (autologous sera) live C. albicans (E:T=1:10) are quantitated in a microtiter ferricytochrome c reduction assay. The assay is performed in the presence of 1% gelatin/HBSS and 80 $\mu$M ferricytochrome c in a total volume of 200 $\mu$L/well. The nmoles of cytochrome c reduced/well is calculated from spectrophotometric readings (550 nm) taken following a 1 hour incubation at 37 ° C. (5% $CO_2$). The amount of SOD-inhibitable cytochrome c reduced is determined by the inclusion of wells containing SOD (200 U/well). Baseline superoxide release is determined in the absence of stimuli. Experimental data are expressed as a percentage of the control group.

We claim:

1. The compounds of the invention are represented by structural Formula (I)

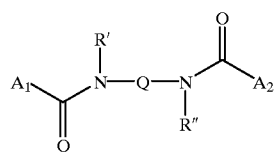

(I)

wherein:
  $A_1$ and $A_2$ independently from each other denote a group $Z(CH_2)k$—$(NR''')q$ wherein: Z is a 4–10 membered mono- or bicyclic heterocyclic ring system containing up to four heteroatoms N, O, S in the ring in which at least one heteroatom is N, and wherein the ring is substituted or unsubstituted by one or two $C_{1-4}$alkyl, F, Cl, Br, I, $C_{1-4}$ alkoxy, $(CH_2)_m R_4$, oxo, oxime, O—$C_{1-4}$alkyloxime, hydroxy, $N(R_3)_2$, acylamino or aminoacyl groups, 8, 9, 10 membered monocyclic ring systems being excluded;
  k is independently an integer from 0 to 4;
  R''' denotes hydrogen, $C_{1-4}$-alkyl or $C_{1-4}$-alkylcarboxylic acid;
  q is independently an integer from 0 to 1;
  R' and R'' are independently hydrogen, $C_{1-4}$alkylC(O)$R_4$, $C_{1-4}$alkyl or R' and R'' are benzyl which is optionally substituted by one or two $C_{1-4}$alkyl, $C_{1-4}$alkoxy, F, Cl, I, Br, OH, or $N(R_3)_2$;
  Q denotes a group

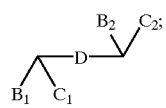

wherein:
  $B_1$ denotes halogen, —$(CH_2)_m$—CN, —$(CH_2)_{m+1}$—$R^2$, —$(CH_2)_m$—$R^3$, —$(CH_2)_m$—$COR^2$ or —$(CH_2)_m$—$COR^3$;

$R^2$ independently denotes —$OR^3$, —$N(R^3)_2$, —$SR^3$;
  $R^3$ is independently hydrogen, $C_1$—$C_4$-alkyl or benzyl;
  m is independently an integer from 0 to 4;
  $C_1$ denotes halogen, —$(CH_2)_n$—CN, —$(CH_2)_{n+1}$—$R^4$, —$(CH_2)_n$—$R^5$, —$(CH_2)_n$—$COR^4$ or —$(CH_2)_n$—$COR^5$;
  $R^4$ independently denotes —$OR^5$, —$N(R^5)_2$, —$SR^5$;
  $R^5$ is independently hydrogen, $C_1$—$C_4$-alkyl or benzyl;
  n is independently an integer from 0 to 4;
  $B_2$ denotes halogen, —$(CH_2)_p$—CN, —$(CH_2)_{k+1}$—$R^6$, —$(CH_2)_k$—$R^7$, —$(CH_2)_k$—$COR^6$ or —$(CH_2)_k$—$COR^7$;
  $R^6$ independently denotes —$OR^7$, —$N(R^7)_2$, —$SR^7$;
  $R^7$ is independently hydrogen, $C_1$—$C_4$-alkyl or benzyl;
  k is an integer from 0 to 4;
  $C_2$ denotes halogen, —$(CH_2)_s$—CN, —$(CH_2)_{s+s}$—$R^8$,—$(CH_2)_s$—$R^9$, —$(CH_2)_s$—$COR^8$ or —$(CH_2)_s$—$COR^9$; where
  $R^8$ independently denotes —$OR^9$, —$N(R^9)_2$, —$SR^9$;
  $R^9$ is independently hydrogen, $C_1$—$C_4$-alkyl or benzyl;
  s is an integer from 0 to 4;
  D is $(CH_2)_i$; in which up to two carbons are optionally gem-substituted by $R^{10}$ and $R^{11}$; where
  $R^{10}$ and $R^{11}$ are independently $C_{1-4}$alkyl, $C_{2-4}$alkenyl, $C_{2-4}$alkynyl; all of which may be substituted by one or two $C_{1-4}$alkyl, OH, F, Cl, Br, I, $N(R^{12})_2$, $(R^{12})_2NC(O)$—, —$(CH_2)_S R^{13}$, —$(CH_2)_S R^{12}$, —$(CH)_2)_S COR^{13,}$ or —$(CH_2)_S C(O)R^{12}$;
  or $R_{10}$ and $R_{11}$ are F, Cl, or Br;
  or $R_{10}$ and $R_{11}$ may together form a cyclic or heterocyclic ring of Formula (Ia):

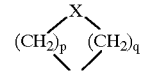

(Ia)

in which p and q are independently an integer from 0 to 3; provided p and q are not both 0;
  X is O, S, $CH_2$ or $N(R^{12})$;
  $R^{12}$ is independently hydrogen, $C_{1-4}$-alkyl or benzyl;
  $R^{11}$ is independently $OR^{12}$, $N(R^{12})_2$ or $SR^{12}$;
  i is an integer from 3 to 8;
  with the proviso that $B_1$ is not identical to $C_1$ and $B_2$ is not identical to $C_2$;

$A_1 \neq A_2$;

$B_1 \neq B_2$;

$C_1 \neq C_2$;

$B_1 \neq C_1$; and $B_2 \neq C_2$;

and pharmaceutically acceptable salts thereof.

2. Compounds according to claim 1, wherein Z denotes an optionally substituted pyrrolyl, isopyrrolyl, pyrazolyl, isoimidazolyl, triazolyl, iosxazolyl, oxazolyl, thiazolyl, isothiazolyl, oxadiazolyl, pyridinyl, pyridazinyl, pyrimidinyl, pyrazinyl, pyrrolidinyl, piperazinyl, triazinyl, morpholinyl, indolyl, indoleninyl, isobenzazolyl, pyrindinyl, ioindazolyl, indoxazinyl, benzoxazolyl, quinolinyl, isoquinolinyl, cinnolinyl, quinazolinyl, naphthyridinyl, pyridopyridinyl, tetrahydroquinolinyl, tetrahydroisoquinolinyl, quinoxalinyl, indolinyl, pyrrolidonyl, imidazolyl, imidazolidinyl, imidazolinyl, piperidyl, tetrazolyl, quinuclidinyl, azetidinyl, or purinyl.

3. Compounds according to claim 1, wherein Z is pyridinyl, pyrinidinyl, pyrazinyl, pyridazinyl, quinolinyl, tetrahydroquinolinyl, azetidinyl, or pyrrolidinyl; $R_{10}$ and $R_{11}$ are $C_{1-4}$alkyl, substituted by $C_{1-4}$ alkyl, OH, $N(R_{12})_2$, —$(CH_2)_sR_{13}$, or —$(CH_2)_sC(O)R_{12}$; or $R_{10}$ and $R_{11}$ may together form a cyclic or heterocyclic ring of Formula (Ia) wherein X is O, S, or $CH_2$; and p and q are 1–3; $R_{12}$ is hydrogen or $C_{1-4}$alkyl; and $R_{13}$ is $OR_{12}$ or $N(R_{12})_2$.

4. Compounds according to claim 1 wherein Z is optionally mono-, poly- or mixed substituted by $C_{1-4}$alkyl, $C_{1-4}$-alkoxy, $C_{1-4}$-alkoxy—$C_{1-4}$-alkyl, oxo, oxime, O—$C_{1-4}$-alkyloxime, hydroxy, amino, $C_{1-4}$alkylamino, di—$C_{1-4}$-alkylamino, acylamino or aminoacyl.

5. Compounds according to claim 1 wherein Z is optionally mono-, poly- or mixed substituted by methyl, ethyl, methoxy, methoxymethyl, oxo, oxime, hydroxy, amino, ethylamino or dimethylamino.

6. Compounds according to claim 1 wherein R' and R" independently from each other denote hydrogen, methyl, ethyl, propyl, butyl, $C_{1-4}$—alkylcarboxylic acid or $C_{2-4}$-alkylhydroxy.

7. Compounds according to claim 1 wherein $B_1$ denotes halogen, —$(CH_2)_mCN$, —$(CH_2)_{m+1}$—$R^2$, —$(CH_2)_m$—$R^3$, —$(CH_2)_m$—$COR^2$ or —$(CH_2)_m$—$COR^3$, where $R^2$ denotes —$OR^3$, —$NR^3{}_2$, —$SR^3$, and $R^3$ is hydrogen, methyl, ethyl, propyl, i-propyl, butyl or benzyl and m is an integer from 0 to 4.

8. Compounds according to claim 1 wherein $C_1$ denotes halogen, —$(CH_2)_n$—CN, —$(CH_2)_{n+1}$—$R^4$, —$(CH_2)_n$—$R^5$, —$(CH_2)_n$—$COR^4$ or —$(CH_2)_n$—$COR^5$, where $R^4$ denotes —$OR^5$, —$NR^5{}_2$, —$SR^5$, and $R^5$ is hydrogen, methyl, ethyl, propyl, i-propyl, butyl or benzyl and n is an integer from 0 to 4.

9. Compounds according to claim 1 wherein $B_2$ denotes halogen, —$(CH)_p$—CN, —$(CH_2)_{p+1}$—$R^6$, —$(CH_2)_p$—$R^7$, —$(CH_2)_p$—$COR^6$ or —$(CH_2)_p$—$COR^7$, where $R^6$ denotes —$OR^7$, —$NR^7{}_2$, —$SR^7$, and $R^7$ is hydrogen, methyl, ethyl, propyl, i-propyl, butyl or benzyl and p is an integer from 0 to 4.

10. Compounds according to claim 1 wherein $C_2$ denotes halogen, —$(CH_2)_1$—CN, —$(CH_2)_{1+1}$—$R^8$, —$(CH_2)_1$—$R^9$, —$(CH_2)_1$—$COR^8$ or —$(CH_2)_1$—$COR^9$, where $R^8$ denotes —$OR^9$, —$NR^9{}_2$, —$SR^9$, and $R^9$ is hydrogen, methyl, ethyl, propyl, i-propyl, butyl or benzyl and 1 is an integer from 0 to 4.

11. A pharmaceutical composition comprising a compound according to claim 1 and a pharmaceutically acceptable carrier.

12. A method of stimulating the myelopoietic system which comprises administering to a subject in need thereof, an effective amount to stimulate said myelopoietic system of a compound of claim 1.

13. A method of preventing or treating sepsis which comprises administering to a subject in need thereof, an effective amount of a compound of claim 1.

14. A method of preventing or treating viral, fungal and bacterial infections which comprises administering to a subject in need thereof, an effective amount of a compound of claim 1.

* * * * *